United States Patent
Chiu et al.

(10) Patent No.: US 6,666,880 B1
(45) Date of Patent: Dec. 23, 2003

(54) METHOD AND SYSTEM FOR SECURING A COATED STENT TO A BALLOON CATHETER

(75) Inventors: Jessica Chiu, Belmont, CA (US); Keith Edward Fong, Palo Alto, CA (US)

(73) Assignee: Advised Cardiovascular Systems, Inc., Santa Clara, CA (US)

(*) Notice: Subject to any disclaimer, the term of this patent is extended or adjusted under 35 U.S.C. 154(b) by 276 days.

(21) Appl. No.: 09/885,594

(22) Filed: Jun. 19, 2001

(51) Int. Cl.[7] .................................................. A61F 2/06
(52) U.S. Cl. ..................................... 623/1.11; 606/194
(58) Field of Search ................................ 606/191, 192, 606/194, 195, 198; 623/1.11, 1.12, 1.23, 1.36, 1.42, 1.43

(56) References Cited

U.S. PATENT DOCUMENTS

| | | |
|---|---|---|
| 2,701,559 A | 2/1955 | Cooper |
| 4,323,071 A | 4/1982 | Simpson et al. |
| 4,338,942 A | 7/1982 | Fogarty |
| 4,439,185 A | 3/1984 | Lundquist |
| 4,516,972 A | 5/1985 | Samson |
| 4,538,622 A | 9/1985 | Samson et al. |
| 4,554,929 A | 11/1985 | Samson et al. |
| 4,573,470 A | 3/1986 | Samson et al. |
| 4,608,984 A | 9/1986 | Fogarty |
| 4,616,652 A | 10/1986 | Simpson |

(List continued on next page.)

FOREIGN PATENT DOCUMENTS

| | | |
|---|---|---|
| EP | 0 553 960 A1 | 8/1993 |
| EP | 0 834 293 A1 | 4/1998 |
| EP | 0 974 315 A1 | 1/2000 |
| EP | 0 1 034 752 A1 | 9/2000 |
| FR | 2 753 907 | 4/1998 |
| SU | 1477423 | 5/1989 |
| WO | WO 95/33422 | 12/1995 |
| WO | WO 98/07390 | 2/1998 |
| WO | WO 01/17459 A1 | 3/2001 |

OTHER PUBLICATIONS

ACS RX Multi-Link™ Coronary Stent System Brochure (Undated), 7 pages.

Primary Examiner—Julian W. Woo
Assistant Examiner—Jessica R Baxter
(74) Attorney, Agent, or Firm—Fulwider Patton Lee & Utecht, LLP

(57) ABSTRACT

A method for mounting coated stents on balloon catheters uses a sheath and a pressurized fluid to expand the balloon. Heat is applied only at the ends of the balloon. An insulating disk and a chill block prevent overheating of the temperature sensitive stent coatings.

38 Claims, 4 Drawing Sheets

U.S. PATENT DOCUMENTS

| | | | |
|---|---|---|---|
| 4,638,805 A | 1/1987 | Powell | |
| 4,702,252 A | 10/1987 | Brooks et al. | |
| 4,733,665 A | 3/1988 | Palmaz | |
| 4,748,982 A | 6/1988 | Horzewski et al. | |
| 4,880,683 A | 11/1989 | Stow | |
| 4,950,227 A | 8/1990 | Savin et al. | |
| 4,994,033 A | 2/1991 | Shockey et al. | |
| 5,037,392 A | 8/1991 | Hillstead | |
| 5,059,169 A | 10/1991 | Zilber | |
| 5,064,435 A | 11/1991 | Porter | |
| 5,078,720 A | 1/1992 | Burton et al. | |
| 5,100,429 A | 3/1992 | Sinofsky et al. | |
| 5,108,416 A | 4/1992 | Ryan et al. | |
| 5,116,318 A | 5/1992 | Hillstead | |
| 5,147,370 A * | 9/1992 | McNamara et al. | 623/1.11 |
| 5,156,911 A | 10/1992 | Stewart | |
| 5,158,548 A | 10/1992 | Lau et al. | |
| 5,226,889 A | 7/1993 | Sheiban | |
| 5,242,399 A | 9/1993 | Lau et al. | |
| 5,254,091 A * | 10/1993 | Aliahmad et al. | 606/194 |
| 5,344,426 A | 9/1994 | Lau et al. | |
| 5,360,401 A | 11/1994 | Turnland | |
| 5,387,450 A | 2/1995 | Stewart | |
| 5,409,495 A | 4/1995 | Osborn | |
| 5,412,035 A | 5/1995 | Schmitt et al. | |
| 5,445,646 A | 8/1995 | Euteneuer et al. | |
| 5,451,233 A | 9/1995 | Yock | |
| 5,456,713 A * | 10/1995 | Chuter | 623/1.23 |
| 5,458,615 A | 10/1995 | Klemm et al. | |
| 5,476,476 A | 12/1995 | Hillstead | |
| 5,496,346 A | 3/1996 | Horzewski et al. | |
| 5,501,227 A | 3/1996 | Yock | |
| 5,507,768 A | 4/1996 | Lau et al. | |
| 5,514,154 A | 5/1996 | Lau et al. | |
| 5,545,209 A * | 8/1996 | Roberts et al. | 623/1.11 |
| 5,571,135 A | 11/1996 | Fraser et al. | |
| 5,645,559 A | 7/1997 | Hachtman et al. | |
| 5,653,691 A | 8/1997 | Rupp et al. | |
| 5,667,523 A | 9/1997 | Bynon et al. | |
| 5,695,498 A | 12/1997 | Tower | |
| 5,700,286 A | 12/1997 | Tartaglia et al. | |
| 5,720,726 A | 2/1998 | Marcadis et al. | |
| 5,746,745 A | 5/1998 | Abele et al. | |
| 5,759,474 A | 6/1998 | Rupp et al. | |
| 5,810,871 A | 9/1998 | Tuckey et al. | |
| 5,830,179 A * | 11/1998 | Mikus et al. | 606/198 |
| 5,830,217 A | 11/1998 | Ryan | |
| 5,836,965 A | 11/1998 | Jendersee et al. | |
| 5,843,119 A * | 12/1998 | Shmulewitz | 606/198 |
| 5,846,247 A * | 12/1998 | Unsworth et al. | 606/108 |
| 5,893,852 A | 4/1999 | Morales | |
| 5,976,155 A | 11/1999 | Foreman et al. | |
| 6,027,510 A | 2/2000 | Alt | |
| 6,051,021 A | 4/2000 | Frid | |
| 6,056,906 A | 5/2000 | Werneth et al. | |
| 6,059,810 A | 5/2000 | Brown et al. | |
| 6,063,092 A | 5/2000 | Shin | |
| 6,066,156 A | 5/2000 | Yan | |
| 6,086,610 A | 7/2000 | Duerig et al. | |
| 6,099,559 A | 8/2000 | Nolting | |
| 6,106,530 A | 8/2000 | Harada | |
| 6,110,180 A | 8/2000 | Foreman et al. | |
| 6,123,712 A | 9/2000 | Di Caprio et al. | |
| 6,159,227 A | 12/2000 | Di Caprio et al. | |
| 6,159,229 A * | 12/2000 | Jendersee et al. | 606/198 |
| 6,168,617 B1 | 1/2001 | Blaeser et al. | |
| 6,174,316 B1 | 1/2001 | Tuckey et al. | |
| 6,193,727 B1 | 2/2001 | Foreman et al. | |
| 6,217,586 B1 | 4/2001 | Mackenzie | |
| 6,245,076 B1 | 6/2001 | Yan | |
| 6,258,099 B1 | 7/2001 | Mareiro et al. | |
| 6,277,110 B1 | 8/2001 | Morales | |
| 2001/0016753 A1 | 8/2001 | Caprio et al. | |
| 2003/0055482 A1 * | 3/2003 | Schwager et al. | 623/1.11 |

\* cited by examiner

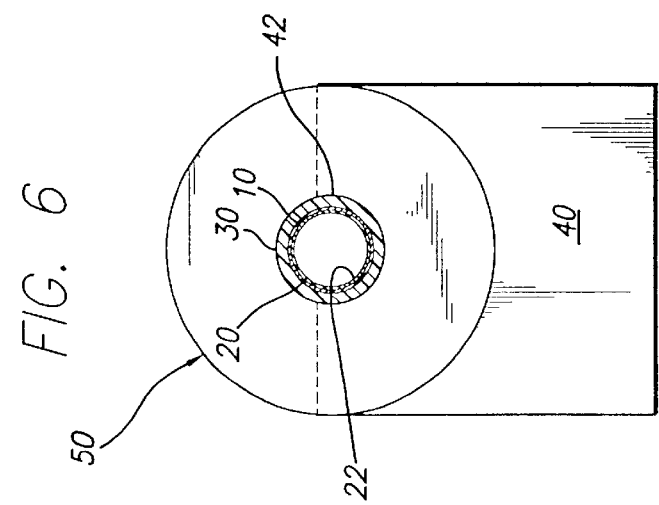
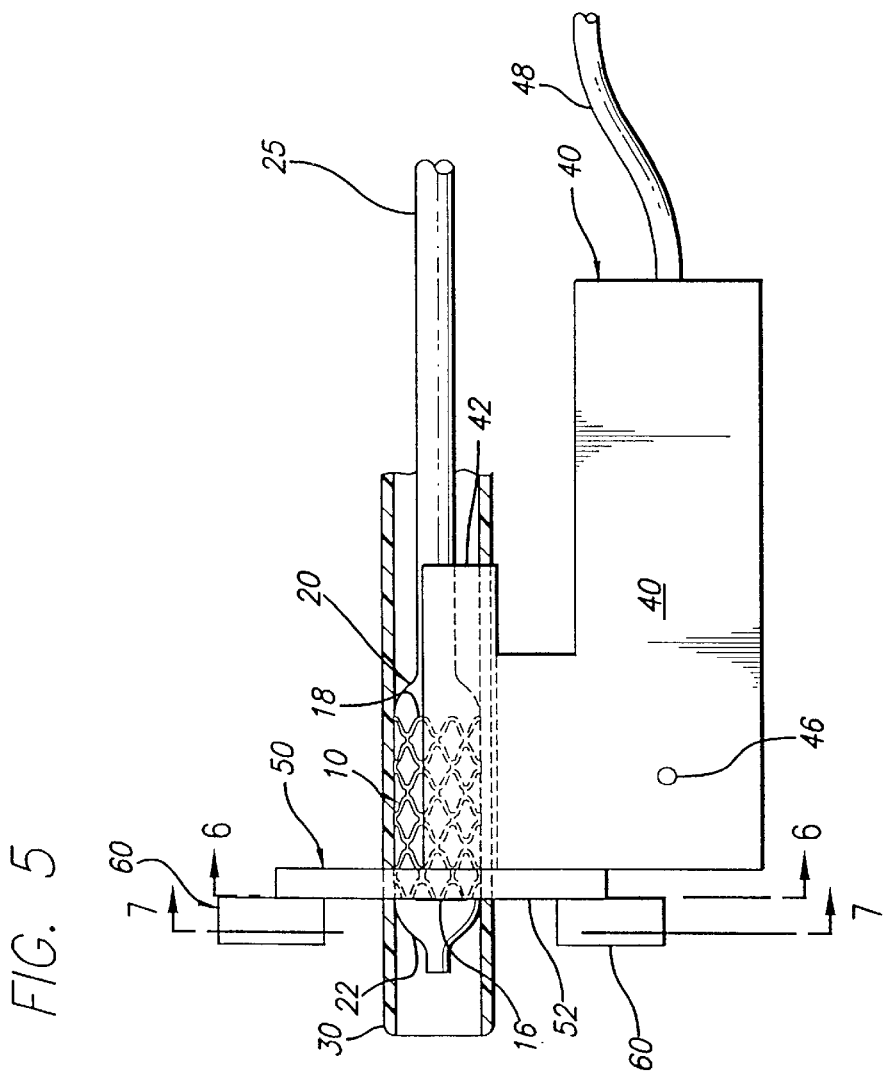

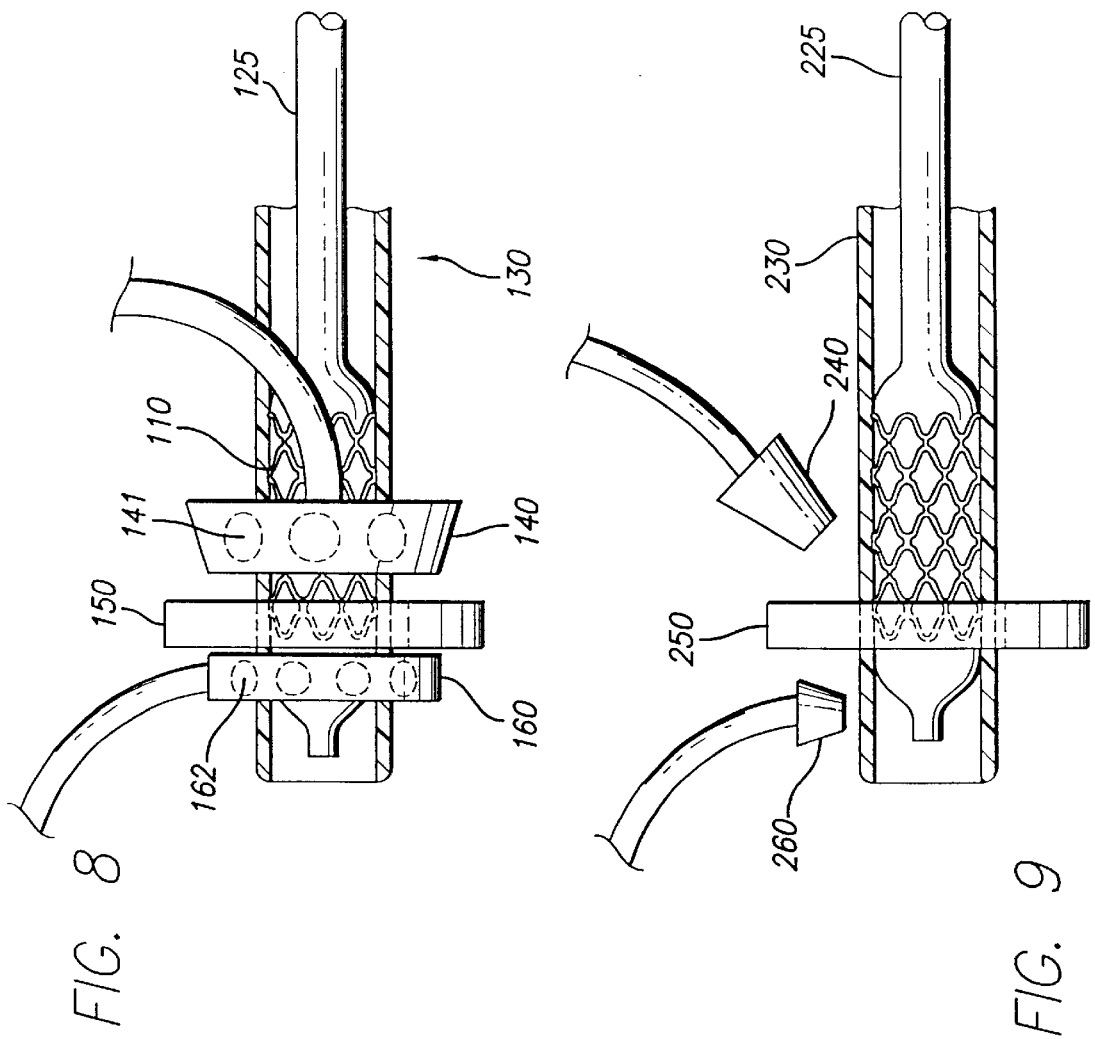

METHOD AND SYSTEM FOR SECURING A COATED STENT TO A BALLOON CATHETER

BACKGROUND OF THE INVENTION

This invention relates to devices for the treatment of heart disease and particularly to stents. More specifically, the invention relates to a method and system for removably securing the stent to a catheter for delivery through a body lumen and subsequent implantation. The invention has particular usefulness in securing stents coated with heat sensitive material.

A variety of non-surgical interventional procedures have been developed over the years for opening stenosed or occluded blood vessels caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty, in which an inflatable balloon is introduced within the stenosed region of the blood vessel to dilate the occluded vessel. The balloon catheter is initially inserted into the patient's arterial system and is advanced and manipulated into the area of stenosis. The balloon is inflated to compress the plaque and press the vessel wall radially outward to increase the diameter of the blood vessel.

In another widely practiced procedure, the stenosis can be treated by placing an expandable interventional instrument such as an expandable stent into the stenosed region to expand and hold open the segment of blood vessel or other arterial lumen. Stents are particularly useful in the treatment or repair of blood vessels after percutaneous transluminal coronary angioplasty (PTCA), percutaneous transluminal angioplasty (PTA), or by atherectomy. Stents are usually delivered to the target site in a compressed, or crimped, condition, and then are deployed into an expanded condition to support the vessel and help maintain it in an open position.

One method and system developed for delivering stents within a patient's body lumen involves crimping a stent about an expandable member, such as an angioplasty balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway.

Retaining the position of the stent in the proper location on the expandable member while advancing the catheter through the body lumen has sometimes proven difficult. If the stent is dislodged from or moved on the expandable member, the system will not correctly deliver the stent into the body lumen.

Different methods have been attempted to maintain the position of the stent on the expandable member. One such method involves a protective sheath surrounding the catheter and stent assembly. The sheath is retracted prior to the inflation of the expandable member. The use of the sheath, however, increases the profile of the catheter assembly and decreases the flexibility of the system. Another method involves removing the friction reducing coating on the expandable member in the location of the stent, thus allowing the catheter assembly's pre-coated surface to hold the stent in frictional contact.

Another method of securing the stent to the balloon catheter is described in U.S. Pat. No. 5,836,965 to Jendersee et al. The method, while not completely clear, appears to include the steps of positioning a stent onto a balloon within an encapsulating sheath, pressurizing the balloon while elevating the temperature of the balloon, depressurizing the balloon, and then removing the encapsulating sheath. In the final configuration the balloon extends through or around a portion of the stent.

A significant improvement to the Jendersee method is described in U.S. application Ser. No. 09/391,859, filed Sep. 8, 1999, to Foreman, Limon, et al. and assigned to Advanced Cardiovascular Systems, Inc., the assignee of the present invention. That application is incorporated by reference in its entirety. It describes how local deformations can be formed in an expandable member, such as a balloon, by forcing an expansion fluid into the interior of the expandable member while the stent is crimped on it. In this manner the expandable member partially inflates into the gaps in the stent. To restrain the expandable member from expanding during deformation of the expandable member, an inelastic sheath can be placed about the stent. The inelastic sheath allows the internal pressures in the expandable member to exceed the levels which would otherwise expand the expandable stent. A further improvement is to heat the expandable member while it is being deformed, to a sufficient temperature and for a sufficient duration to permanently deform the expandable member to form bulges which fill the gaps (i.e.,voids) between the struts of the stent. Advanced Cardiovascular Systems, Inc. (ACS) of Santa Clara, Calif., the assignee of this invention, calls this method the GRIP process, in which a high temperature nozzle traverses the entire length of the stent several times while the sheathed balloon remains pressurized. Nozzle temperatures can approach 200° F.

The advent of coated stents has rendered these prior art methods of stent attachment ineffective. Coated stents, particularly those coated with drugs, are often temperature sensitive, and cannot withstand the heat required in the prior art methods. In the past, one solution would have been to simply sheath the stent, but that is no longer acceptable. The increasing trend to direct stenting—placing the stent without first opening the stenosis by balloon angioplasty—requires lower profile stents while insuring that the stents remain secured to the balloon until placed at the lesion and expanded. With some coatings, sensitive to temperatures of approximately 50° C. (122° F.), like actinomycin-D, no satisfactory method has been developed to use heat in securing crimped stents to balloons.

What has been needed and unavailable is a means of mounting and maintaining a coated stent at a desired location on a stent delivery system while using a heat-seated balloon, but without increasing the overall profile of the catheter assembly and thus compromising flexibility. The present invention satisfies this need.

SUMMARY OF THE INVENTION

This invention is directed to an improved method and system for securing coated stents to delivery systems. Securing the stent is accomplished by tightly crimping the stent onto the balloon portion of a catheter. An expansion restraint is placed over the stent and the balloon is pressurized. The balloon at the end of the stent conforms to the stent's geometry. The stent is kept cool by a stent temperature controller while a portion of the catheter balloon extending beyond the edge of the stent is heated by a heat source, such as hot air. The heat permanently seats the balloon at the stent's ends. In one embodiment, an insulating material is disposed between the heat source and the stent temperature controller to further protect the stent. In this manner, the stent is kept cool enough so that any temperature sensitive coatings are not deleteriously affected while heat is applied to the balloon. The basic system for accomplishing this method includes the heat source, the insulator, and the stent temperature controller.

Additional steps can be added to the method to provide for treating both ends of the balloon and for quenching the balloon once it has been adequately heated. The method is preferably accomplished by using the embodiment of a system for securing the stent that is disclosed in detail below. The system includes a hollow chiller block that is fed cool air from a chiller. The chiller block keeps the stent cool. The block is separated from heat nozzles by a rubber insulating disk. The disk insulates the stent from the heat that the nozzles apply to the end of the balloon protruding out from the stent and beyond the disk.

The present invention results in a simplified method of inserting the stent into the body lumen, because no sheath is required to secure the stent. The catheter assembly is inserted into the body lumen without further steps being taken to secure the stent. The absence of a sheath makes the assembly more flexible than it would be with a sheath. The expandable member is inflated at the desired location, expanding and implanting the stent within the body lumen. When the expandable member is then deflated, the stent is released and the remainder of the catheter assembly may be withdrawn, leaving the stent implanted within the body lumen.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 5 depicts a side elevation view of the invention.

FIG. 6 depicts a cross-sectional view through lines 6—6 of FIG. 5, showing the insulator disk, chill block, and the sheath-restrained stent and balloon catheter assembly.

FIG. 8 depicts another embodiment of the invention with a plurality of cold air nozzles surrounding the stent and balloon.

FIG. 9 depicts another embodiment of the system, with single hot and cold air nozzles.

DETAILED DESCRIPTION OF THE PREFERRED EMBODIMENTS

Figure 1:
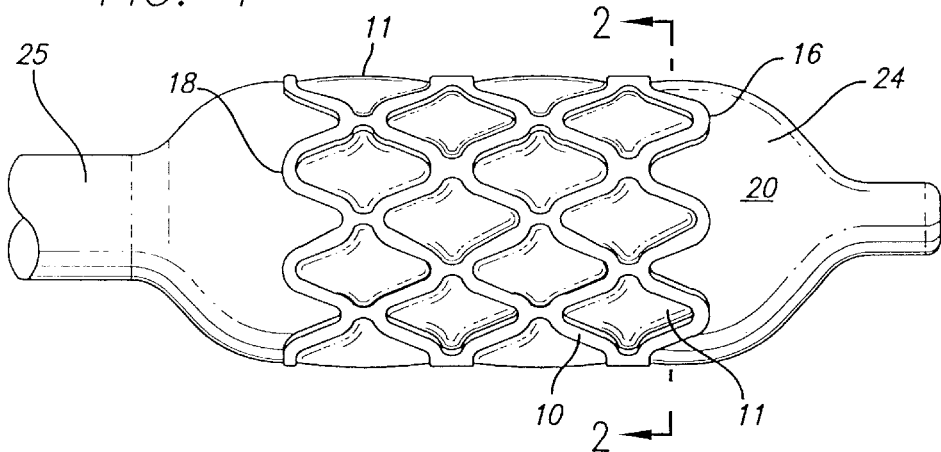
FIG. 1 depicts a partial longitudinal plan view of an expandable member, stent, and catheter assembly.

The present invention provides an apparatus and method for securing a stent on a catheter and is particularly useful in securing a coated stent on a catheter. The apparatus is a system that includes a heat source, such as hot air nozzle, and a temperature controller to keep the stent cool. An insulating material also protects the stent and its coating from the heat. The method of the present invention uses this system to secure an endovascular prosthesis, such as a stent, on the end of a catheter such as a balloon catheter used for angioplasty and stent delivery.

When securing a coated stent on a catheter care must be taken so that the coating is not scratched or disrupted. As part of the stenting procedure, it may be beneficial to coat the stent with a therapeutic drug or agent. The therapeutic agent may perform a variety of functions, from preventing blood clots to promoting healing. As an example, an active agent coated on the stent can inhibit the activity of vascular smooth muscle cells. More specifically, the active agent is aimed at inhibiting abnormal or inappropriate migration and proliferation of smooth muscle cells. The active agent can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of therapeutic agents that are available as stent coatings include rapamycin, actinomycin D (ActD), or derivatives and analogs thereof ActD is manufactured by Sigma-Aldrich, 1001 West Saint Paul Avenue, Milwaukee Wis. 53233, or COSMEGEN, available from Merck. Synonyms of actinomycin D include dactinomycin, actinomycin IV, actinomycin 11, actinomycin X1, and actinomycin C1. Examples of agents include other antiproliferative substances as well as antineoplastic, antinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein, llb/llla platelet membrane receptor antagonist, recombinant hirudin, thrombin inhibitor (available from Biogen), and 7E-3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

Figure 2:
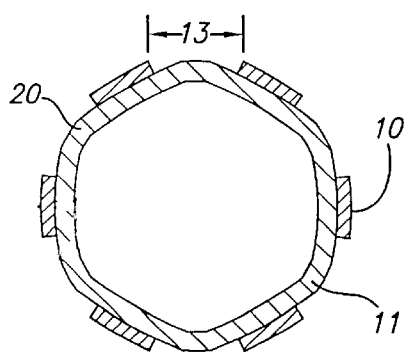
FIG. 2 depicts a cross-sectional view along lines 2—2 of FIG. 1.
Figure 3:
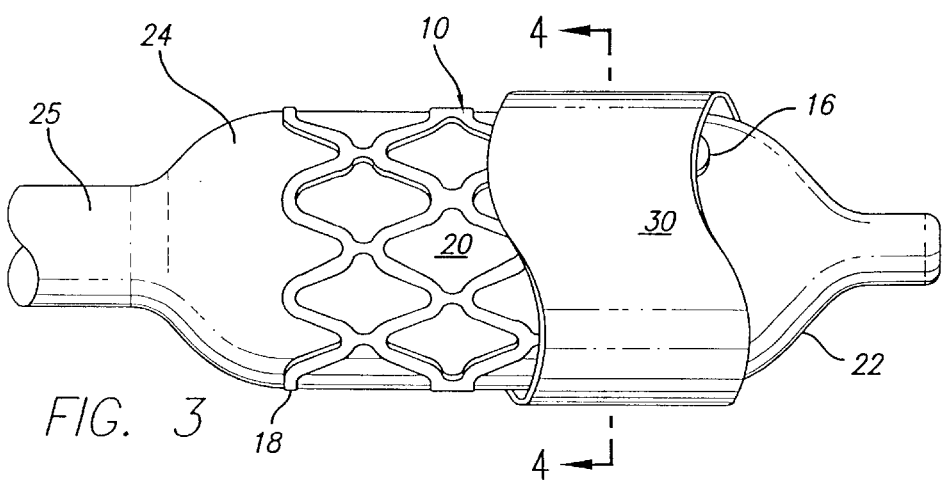
FIG. 3 depicts a partial longitudinal plan view of the expandable member and stent assembly covered by the retaining sheath.

FIGS. 1, 2 and 3 illustrate a catheter 25 containing a stent 10 placed over the outer surface 24 of an expandable member (such as a catheter balloon 20). The stent 10 is tightly crimped about the balloon 20 and is removably secured thereon due to interference between the stent 10 and slight balloon deformations 11. The stent 10, with front end 16 and rear end 18, depicted in the drawings, conceptually represents any stent with a lattice or mesh configuration of expandable material. It is anticipated that stent 10 can, for example, be any of the prior art, existing, or future expandable metal stents known to those of skill in the art.

Figure 4:
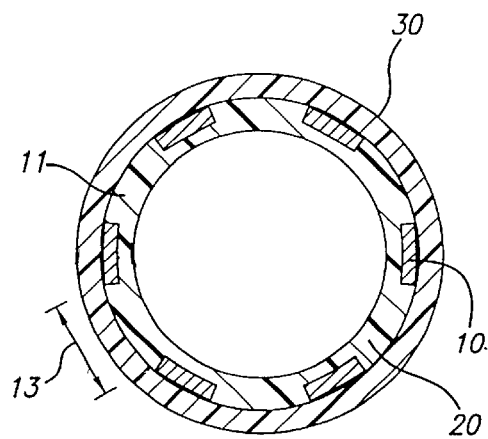
FIG. 4 depicts a cross-sectional view along lines 4—4 of FIG. 3, after the balloon pressurization has begun.

Preferably, as shown in FIG. 3, expansion restraint 30 is placed over expandable stent 10 and expandable member 20 before the expandable member 20 is pressurized. The restraint 30, such as a sheath, is placed so that it entirely encompasses the expandable stent 10 and acts to prevent the stent from expanding while the expandable member is pressurized and thus is deformed, as shown in FIG. 4. Deformation of the balloon 20 to form local deformations 11 to fill gaps 13 in the stent lattice is enhanced by use of the sheath 30. Placing the sheath 30 over the stent 10 allows the pressure of the inflation fluid in the expandable member 20 to exceed the levels which would otherwise cause the stent to expand. It will be understood by those of skill in the art that sheath 30 covers the entire balloon 20, and that FIG. 3 shows only a portion of the sheath for purposes of clarity. The local deformations 11 increase in size and form in the stent gaps 13 as the expandable member starts to expand, but the stent cannot expand because it is restrained by sheath 30. Increased pressure ensures that greater deformations will occur in the expandable member 20 while the expandable stent 10 remains in the unexpanded condition. The sheath 30 is preferably a heat resistant and stretch-resistant polymeric material, such as a Teflon® sheath (e.g. approximately 0.045 inch inside diameter). The diameter of the sheath should be chosen according to the diameter of the stent, which may vary depending on the vessel in which it is implanted (coronary, peripheral, biliary, etc.).

A comparison between FIG. 2 and FIG. 4 illustrates what happens. FIG. 2 represents an unpressurized stent and balloon, crimped but with no restraining sheath. With a sheath, as pressure is applied by an expansion fluid (not shown), balloon 20 expands to look like FIG. 4, with exterior surface 24 of balloon 20 moving into stent gaps 13 while restrained by sheath 30. As an example, a typical final pressure is 275 psi. In this manner expandable member 20 forms larger local deformations 11 in gaps 13, which secure stent 10 by increasing the mechanical bond between outer surface 24 of the expandable member 20 and the expandable stent 10. The result is that balloon 20 conforms to the geometry of stent 10 at the ends of the stent. If section 4—4 of FIG. 3 were taken at the front end 16 or rear end 18 of stent 10, the view would still look like that depicted in FIG. 4.

A purpose of the present invention is to enable heat application to the ends of balloon 20, so that a greater mechanical bond can be formed between the front end 16 of stent 10 and balloon 20. At the same time, the invention protects other portions of the stent, so any stent coatings will not suffer chemical degradation caused by heat. FIG. 5 depicts the general configuration of the system for cooling most of the stent while heat is applied to a pressurized balloon at one end of the stent. Chill block 40 is a stainless steel manifold. Opening 46 is a chilled air inlet, and opening 48 is an air outlet. The air is chilled by a Chilcut II chiller (not shown) made by ITW Vortec of Cincinnati, Ohio. A portion of the chill block 40 has a curved notch or surface 42 into which fit the assembly of the stent 10, balloon 20, catheter 25, and expansion restraint or Teflon® sheath 30.

On one end of the chill block 40, a heat nozzle 60 is placed near the edge of chill block 40, so that the nozzle 60 can apply hot air to the front end 22 of balloon 20. Heat nozzle 60 is connected to a heat source capable of providing hot air (e.g. between the temperatures of 180° and 200° F. about 82° C. to about 94° C. at the nozzle). In practice, stent 10 may be coated with a therapeutic agent, e.g., a cytotoxic material such as actinomycin-D. At temperatures exceeding 50° centigrade (about 122° F.), the actinomycin-D coating would be affected by the heat from nozzle 60, causing the coating to chemically degrade. To prevent heat nozzle 60 from damaging the stent coating, an insulating disc 50 is interposed between the chill block 40 and heat nozzle 60. Preferably, the insulating disc is made of rubber that is about 0.0625 to 0.125 inch thick. The insulating disc 50 and the chill block 40 prevent the coating on stent 10 from reaching too high a temperature. A temperature differential of approximately 30° C. (about 54° F.) has been maintained between the heat nozzle 60 and the temperature of the stent 10 on chill block 40. It is anticipated that a temperature differential of at least 50° C. (about 90° F.) can be reached. The temperature differential is a function of the amount of heat applied by nozzle 60, the thickness and type of material of the insulating disc 50, and the nature of the stent temperature controller, which in the preferred embodiment is chill block 40. These parameters, in turn, are a function of the heat sensitivity of the stent coating. The stent must be kept a temperature lower than the point at which the coating will degrade. In practice, the front edge 16 of stent 10 is placed approximately even with the heat side face 52 of insulating disc 50. Coated stents that are secured according to the present invention may also involve securing the stent by moving grip sheath 30 (including the balloon 20 and stent 10) in one direction or another along the longitudinal axis of the stent. That axis would be concurrent with catheter 25.

Figure 7:
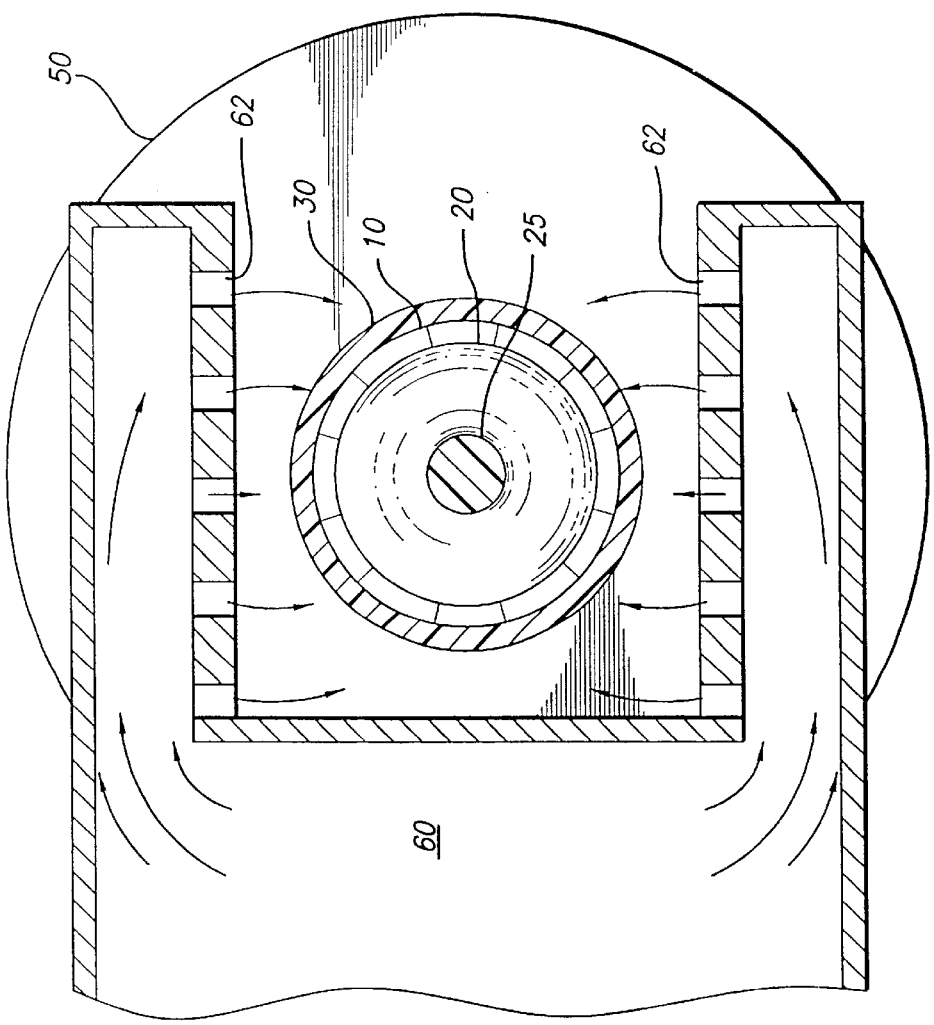
FIG. 7 is a cross-sectional view through lines 7—7 of FIG. 5, showing the hot air nozzle.

FIG. 7 depicts the heat nozzle 60 with hot air outlets 62 both above and below grip sheath 30. The number of hot air outlets 62, and their location, will be a function of the heat necessary to secure the balloon end 22 to stent 10.

To secure the balloon and stent properly, it is preferred that heat be applied to both ends of balloon 20. The preceding discussion has addressed applying heat only at one end. A variety of systems and methods will permit the use of the present invention to secure both ends of the coated stent to the catheter balloon. One way is to simply remove the sheath, stent, balloon, and catheter assembly and reverse it, so that the opposite end of the balloon is heated and the stent secured. Alternatively, two heat nozzles could be secured at a distance approximately equal to the length of the stent. Thus, one embodiment of the invention can include a system which incorporates a single chill block or other stent temperature controller with a heat nozzle and insulating disc at each end of the chill block. In fact, one might choose to heat any particular part of the stent while cooling the other part. The specific details are a matter of choice for one of ordinary skill in the art.

From the preceding description of the catheter assembly, stent, and heating and chilling equipment, it is easy to understand the preferred method of the present invention. A stent is crimped on a catheter balloon. The method of crimping is not material, and can be accomplished by any of the known or proprietary methods available to stent manufacturers. A Teflon® sheath is placed over the balloon. In the preferred method, the sheathed assembly is first pressurized and then secured in the chiller block, although those steps can be reversed. In the present embodiment, the heat nozzle remains stationary, while the chiller block and insulating disk are moveable. The movement can be controlled with a hydraulic system, robotics, or other methods known to those of skill in the art. Once the sheathed assembly is secured in the curved surface 42 of the top of chill block 40 and pressurized, it is moved toward and positioned near the heat nozzle. Other versions of the method contemplate that the pressurization can be accomplished before, during, or after the movement, depending on the choice of manufacturing process. Similarly, whether the heat nozzle operates continually or is shut off while switching from catheter to catheter will depend on the speed and economics of the system.

Heat is ultimately applied to the balloon end, at a nozzle temperature of approximately 90° C. (about 194° F.) for two minutes. The balloon end is then quenched with cool air, approximately 20° C. (about 68° F.) for thirty seconds. The quenching air (or any other gas) can be supplied by the same chiller that cools the chill block, or it can come from a different source. It is also a matter of choice whether to quench before the catheter and sheathed assembly are moved away from the heat nozzle, or after. The preferred method contemplates quenching immediately after heating and before depressurization and movement of stent, balloon, and catheter assembly.

While the invention has been illustrated and described above, it will be apparent to those skilled in the art that variations of the described system and methods can be used. Particular sizes, dimensions, materials, and equipment have been described only for the purpose of providing examples. Other modifications and improvements may be made without departing from the scope of the invention.

For example, one preferred embodiment of the invention contemplates the use of chill block 40, as previously described. Nevertheless, other stent temperature controllers are easily envisioned. For example, FIG. 8 depicts a manifold 140 with numerous outlets 141 for blowing cold air on the stent 110 in the vicinity of the insulating disc 150. The stent 110 actually fits inside or through the manifold 140, so that chilled air can be blown through nozzles 141 and onto the stent. Meanwhile, on the other side of insulating disk 150, outlets 162 of hot air nozzle 160 provide heat at the front end of stent 110. This contrasts with the embodiment shown in FIGS. 5 and 6, in which the Teflon® sheath 30, with stent 10 and balloon 20, are in physical contact with the exterior of the chill block 40. In FIG. 9, the stent temperature controller 240 is even less sophisticated, and simply is a tube with chilled air fed through a nozzle or nozzles and directed toward where grip sheath 230 meets insulating disc 250. Heat nozzle 260 applies heat to the front end of the balloon.

Similarly, stent 10 in FIG. 5 should not be limited in terms of its physical configuration or its constituent materials. Any stent subject to balloon expansion, such as those stents described in the *Handbook of Coronary Stents* by Patrick Serruys and Michael J. B. Kutryk, can be used with the present invention. The same can be said of the catheters and balloons that are depicted in the attached drawings.

As presently envisioned, the securing system depicted in FIG. 5 contemplates that the heat nozzle will remain stationary, and that the grip sheath, balloon, and stent, will be secured to the chill block and moved into place as depicted in FIGS. 5–7. Such movement can be accomplished in any number of ways that are well known in the art. Another variation within the scope of the invention would be to secure an insulating wall in the vicinity of the heat nozzle. Presently, one preferred embodiment of the invention has the sheath, stent, and catheter assembly sitting in a curved notch 42 at the top of chill block 40. Other methods of keeping the stent and chill block in contact, such as straps or clamps, could also be used.

What is claimed is:

1. A method for mounting a stent on a delivery system, comprising the steps of:

providing a catheter assembly having an expandable member with a first end and a second end;

providing an expandable stent having a first end and a second end corresponding to the first and second ends of the expandable member;

crimping the stent on the expandable member so that the first and second ends of the expandable member extend beyond the first and second ends of the stent;

placing an expansion restraint over the stent and at least a portion of the catheter assembly;

pressurizing the catheter assembly and the expandable member to a predetermined pressure;

disposing the expansion restraints, stent, catheter assembly, and expandable member in operative connection with a stent temperature controller and a heat source;

applying heat from the heat source to a portion of the expandable member while controlling the temperature of the stent with the temperature controller;

depressurizing the catheter assembly and expandable member; and removing the expansion restraint.

2. The method of claim 1, further comprising the step of quenching the heated portion of the expandable member before depressurizing the expandable member.

3. The method of claim 2, wherein the heat is applied to the first end of the expandable member.

4. The method of claim 3, further comprising the steps of heating and quenching the second end of the expandable member.

5. The method of claim 1, wherein the stent temperature controller and the heat source are separated by an insulating material.

6. The method of claim 1, wherein the temperature controller comprises a manifold cooled by a chilled fluid.

7. The method of claim 1, wherein the stent is coated with a therapeutic agent prior to the crimping procedure.

8. A method for mounting a coated stent on a delivery system, comprising the steps of:

providing a catheter assembly having a catheter balloon with a first end and a second end;

providing a coated stent having a first end and a second end corresponding to the first and second ends of the catheter balloon;

crimping the coated stent on the catheter balloon so that the first and second ends of the catheter balloon extend beyond the first and second ends of the stent;

placing an expansion restraint over the stent and at least a portion of the catheter assembly;

pressurizing the catheter assembly, including the balloon, to a predetermined pressure;

disposing the expansion restraint, stent, and catheter assembly in operative connection with a stent temperature controller separated from a heat source by an insulator;

applying heat from the heat source to the first end of the catheter balloon while controlling the temperature of the coated stent;

quenching the heated end of the balloon;

depressurizing the catheter assembly and balloon; and removing the expansion restraint.

9. The method of claim 8, further comprising the steps of heating and quenching the second balloon end before depressurizing the catheter assembly and the balloon.

10. The method of claim 9, wherein the second balloon end is heated and quenched after the first balloon end has been heated and quenched.

11. The method of claim 8, wherein the stent temperature controller is a metal manifold, with an interior and an exterior, in operative communication with a source of chilled fluid.

12. The method of claim 11, wherein the chilled fluid is air.

13. The method of claim 12, wherein the chilled air is pumped into the interior of the manifold to chill the exterior of the manifold.

14. The method of claim 13, wherein the heat source is a nozzle with a plurality of openings for directing a heated gas.

15. The method of claim 14, wherein the insulator is one of either rubber or a polymer material.

16. The method of claim 8, wherein a therapeutic agent is coated onto the stent prior to the crimping procedure.

17. A method for securing a coated stent to a balloon catheter, comprising the steps of:

providing an assembly of a pressurized catheter and balloon with end portions, the balloon being covered by a crimped, coated stent and an expansion restraint with the balloon end portions extending beyond the stent;

providing a chill block separated from a heat source by an insulator;

placing the assembly such that the stent is disposed primarily in proximity to the chill block while one end portion of the balloon is disposed proximate to the heat source;

heating and quenching the balloon end portion; and depressurizing the assembly and removing the restraint.

18. The method of claim 17, wherein the heat source produces heated air between the temperatures of 50° C. and 100° C.

19. The method of claim 17, wherein the heated balloon portion is approximately 15° C. to 50° C. warmer than the stent disposed proximate to the chill block.

20. A system for securing stents to balloon catheters, comprising:

a stent temperature controller adapted to chill the temperature of an assembly including a catheter balloon and a stent;

a heat source, disposed proximate the temperature controller, and adapted to heat an end portion of the balloon projecting from an end of the stent; and an insulator disposed between the heat source and the stent temperature controller, the insulator adapted to permit relative motion of the assembly, stent, and expansion restraint.

21. The system of claim 20, wherein the stent temperature controller is a metal manifold.

22. The system of claim 21, wherein the manifold is adapted to hold the catheter assembly, stent, and expansion restraint.

23. The system of claim 20, wherein the metal manifold is chilled by cold air.

24. The system of claim 20, wherein the heat source comprises a plurality of hot air nozzles.

25. The system of claim 20, wherein the insulator is rubber approximately 0.0625 to 0.125 inch thick.

26. The system of claim 20, further comprising an expansion restraint in the balloon and stent assembly.

27. The system of claim 26, wherein the expansion restraint is a Teflon® sheath.

28. The system of claim 20, further comprising a means for quenching the heated balloon end portion.

29. The system of claim 28, wherein a chiller provides cold air to both the stent temperature controller and the quenching means.

30. The system of claim 20, wherein the stent temperature controller comprises chilled air blown on the assembly.

31. The system of claim 20, wherein the stent is coated with a therapeutic agent prior to chilling the stent.

32. A method for securing an endoluminal prosthesis to a flexible expansion device, comprising:

providing an assembly of the prosthesis mounted on the expansion device; and heating at least one end of the flexible expansion device and simultaneously cooling one part of the prosthesis.

33. The method of claim 32, wherein the prosthesis is a stent and the expansion device is an angioplasty balloon.

34. The method of claim 32, further comprising the step of placing an expansion restraint over the assembly and pressurizing the expansion device.

35. The method of claim 34, wherein the temperature differential between two parts of the assembly is 15° C. to 50° C.

36. A method for securing an endoluminal prosthesis to a flexible expansion device, comprising:

providing an assembly of the prosthesis mounted on the expansion device; and heating one part of the assembly with a gas and simultaneously cooling a second part of the assembly with a gas.

37. The method of claim 36, wherein the gas is a gaseous mixture of nitrogen and oxygen and trace gases.

38. The method of claim 37, wherein the gaseous mixture is air.

* * * * *

UNITED STATES PATENT AND TRADEMARK OFFICE
CERTIFICATE OF CORRECTION

PATENT NO. : 6,666,880 B1
DATED : December 23, 2003
INVENTOR(S) : Jessica Chiu and Keith Edward Fong It is certified that error appears in the above-identified patent and that said Letters Patent is hereby corrected as shown below:

<u>Title page,</u>
Item [73], Assignee, delete "Advised", and insert -- Advanced --.

Signed and Sealed this

Fifteenth Day of June, 2004

JON W. DUDAS
*Acting Director of the United States Patent and Trademark Office*